United States Patent
Kuczynski et al.

(10) Patent No.: US 10,405,541 B2
(45) Date of Patent: *Sep. 10, 2019

(54) ENCAPSULATED PAYLOADS BONDED TO POLYMERIC MATERIALS

(71) Applicant: International Business Machines Corporation, Armonk, NY (US)

(72) Inventors: Joseph Kuczynski, North Port, FL (US); Jason T. Wertz, Pleasant Valley, NY (US); Jing Zhang, Poughkeepsie, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/693,027

(22) Filed: Apr. 22, 2015

(65) Prior Publication Data

US 2016/0311992 A1    Oct. 27, 2016

(51) Int. Cl.
  *C08J 7/12*       (2006.01)
  *A01N 25/28*      (2006.01)
  *C11B 9/00*       (2006.01)
  *D06M 23/12*      (2006.01)
  *D06M 101/06*     (2006.01)

(52) U.S. Cl.
  CPC ............... *A01N 25/28* (2013.01); *C08J 7/12* (2013.01); *C11B 9/00* (2013.01); *D06M 23/12* (2013.01); *C08J 2300/106* (2013.01); *C08J 2401/02* (2013.01); *D06M 2101/06* (2013.01); *D06M 2400/01* (2013.01)

(58) Field of Classification Search
  CPC ......... A01N 25/28; C11B 9/00; D06M 23/12; C08J 7/12; C08J 2800/106; C08J 2401/02; A61K 2800/57
  See application file for complete search history.

(56) References Cited

U.S. PATENT DOCUMENTS

| | | |
|---|---|---|
| 4,156,669 A | 5/1979 | Lee |
| 6,028,472 A | 2/2000 | Nagumo |
| 8,512,728 B2 | 8/2013 | Ladet et al. |
| 8,535,477 B2 | 9/2013 | Ladet et al. |
| 8,747,999 B2 | 6/2014 | Grey et al. |
| 2004/0014933 A1* | 1/2004 | Wudl ................. C08F 2/60 528/365 |
| 2009/0297609 A1 | 12/2009 | Shoichet et al. |
| 2013/0059988 A1* | 3/2013 | Palmese ............ C08J 5/04 525/533 |
| 2013/0217572 A1 | 8/2013 | Verheesen et al. |
| 2016/0309710 A1 | 10/2016 | Kuczynski et al. |

FOREIGN PATENT DOCUMENTS

| | | | |
|---|---|---|---|
| CN | 102459556 A | 5/2012 | |
| JP | 2000143379 A | 5/2000 | |
| WO | WO 2013013829 A1 * | 1/2013 | ............ B29C 73/18 |

OTHER PUBLICATIONS

Pratama et al (Nov. 11, 2013). "Room Temperature Self-healing Thermoset Based on the Diels Alder Reaction." ACS Appl. Mater. Interfaces, 5: 12425-12431.*
Zhang et al (Apr. 16, 2014). "Development of self-healing polymers via amine-epoxy chemistry: II. Systematic evaluation of selfhealing performance." Smart Mater. Struct., 23:1-10.*
List of IBM Patents or Patent Applications Treated as Related, Jun. 8, 2015.
Voncina, B. et al. "Encapsulation of Rosemary Oil in Ethylcellulose Microcapsules", Department of Textile Materials and Design, vol. 1, No. 1, 2009, pp. 13-19.
"Surface Modified Microcapsules for Better Adhesion", InnoCentive Challenge, viewed Apr. 13, 2015, 1 page.
Brown, et al., "In situ poly(urea-formaldehyde) microencapsulation of dicyclopentadiene",Journal of Microencapsulation, Nov.-Dec. 2003, vol. 20, No. 6, Taylor & Francis healthsciences, pp. 719-730.

* cited by examiner

*Primary Examiner* — Doan T Phan
(74) *Attorney, Agent, or Firm* — Patterson + Sheridan, LLP

(57) ABSTRACT

In an example, a process for bonding a microcapsule having an encapsulating payload to a polymeric material. The process includes applying a microcapsule (having the encapsulated payload) that includes a dienophile functional group to a polymeric material that includes a diene functional group. The process further includes bonding the microcapsule having the encapsulated payload to the polymeric material via a chemical reaction of the dienophile functional group with the diene functional group.

20 Claims, 6 Drawing Sheets

ENCAPSULATED PAYLOADS BONDED TO POLYMERIC MATERIALS

I. FIELD OF THE DISCLOSURE

The present disclosure relates generally to encapsulated payloads bonded to polymeric materials.

II. BACKGROUND

Microcapsules may be used as release systems for various types of materials (also referred to as "payloads"). Examples of payloads may include perfume oils, repellants, self-healing agents, or disinfecting agents, among other alternatives. Rupturing the microcapsule, and release of the payload, may depend on mechanically breaking a polymer shell of the microcapsule. For example, the polymer shell may be broken by scratching, puncturing, or other mechanical means directly applied to a polymeric surface of the microcapsule. When the microcapsule is coupled to a polymer such as a fiber, it may be difficult to break the polymer shell via direct application of mechanical force. Further, there may be challenges associated with adhering the microcapsules to the polymer, such as the fiber.

III. SUMMARY OF THE DISCLOSURE

According to an embodiment, a process for bonding a microcapsule having an encapsulated payload to a polymeric material is disclosed. The process includes applying a microcapsule (having an encapsulated payload) that includes a dienophile functional group to a polymeric material that includes a diene functional group. The process further includes bonding the microcapsule (having the encapsulated payload) to the polymeric material via a chemical reaction of the dienophile functional group with the diene functional group.

According to another embodiment, a process of modifying a first polymeric material to form a second polymeric material is disclosed. The process includes de-bonding a first microcapsule that is reversibly bonded to a polymeric substrate of a first polymeric material to form a diene-functionalized polymeric substrate. The process includes applying a second microcapsule having an encapsulated payload to the diene-functionalized polymeric substrate. The second microcapsule includes a dienophile functional group. The process further includes forming a second polymeric material by bonding the second microcapsule (having the encapsulated payload) to the polymeric substrate via a chemical reaction of the dienophile functional group with a diene functional group of the diene-functionalized polymeric substrate.

According to another embodiment, a polymeric material is disclosed. The polymeric material includes a fibrous substrate, a cyclic compound, and a microcapsule having an encapsulated payload. The cyclic compound is chemically bonded to the fibrous substrate, and the microcapsule (having the encapsulated payload) is reversibly bonded to the fibrous substrate via the cyclic compound.

One advantage of the present disclosure is the ability to improve adhesion of a microcapsule (having an encapsulated payload) to a polymeric material, such as natural fibers (e.g., cotton fibers) and/or synthetic fibers (e.g., polyester fibers). A microcapsule (having an encapsulated payload) may be functionalized to include a dienophile functional group (e.g., during synthesis of the microcapsule). A polymeric material may be functionalized to include a diene functional group for chemical reaction with the dienophile functional group. A chemical reaction of the dienophile functional group with the diene functional group results in the microcapsule (having the encapsulated payload) being bonded to the polymeric material.

Another advantage of the present disclosure is the ability to de-bond (e.g., via a retro Diels-Alder reaction) a first microcapsule that is reversibly bonded to a polymeric substrate of a first polymeric material. After de-bonding the first microcapsule, a second microcapsule may be chemically bonded to the polymeric substrate to form a second polymeric material. As an example, the first microcapsule may have a first encapsulated payload, and the second microcapsule may have a second encapsulated payload. In some cases, the second encapsulated payload may be the same as the first encapsulated payload in order to replenish a payload material (or multiple payload materials) that may be released as a result of a microcapsule being ruptured. In other cases, the second encapsulated payload may be a different payload in order to provide alternative and/or additional functionality.

Features and other benefits that characterize embodiments are set forth in the claims annexed hereto and forming a further part hereof. However, for a better understanding of the embodiments, and of the advantages and objectives attained through their use, reference should be made to the Drawings and to the accompanying descriptive matter.

IV. BRIEF DESCRIPTION OF THE DRAWINGS

V. DETAILED DESCRIPTION

Figure 1:
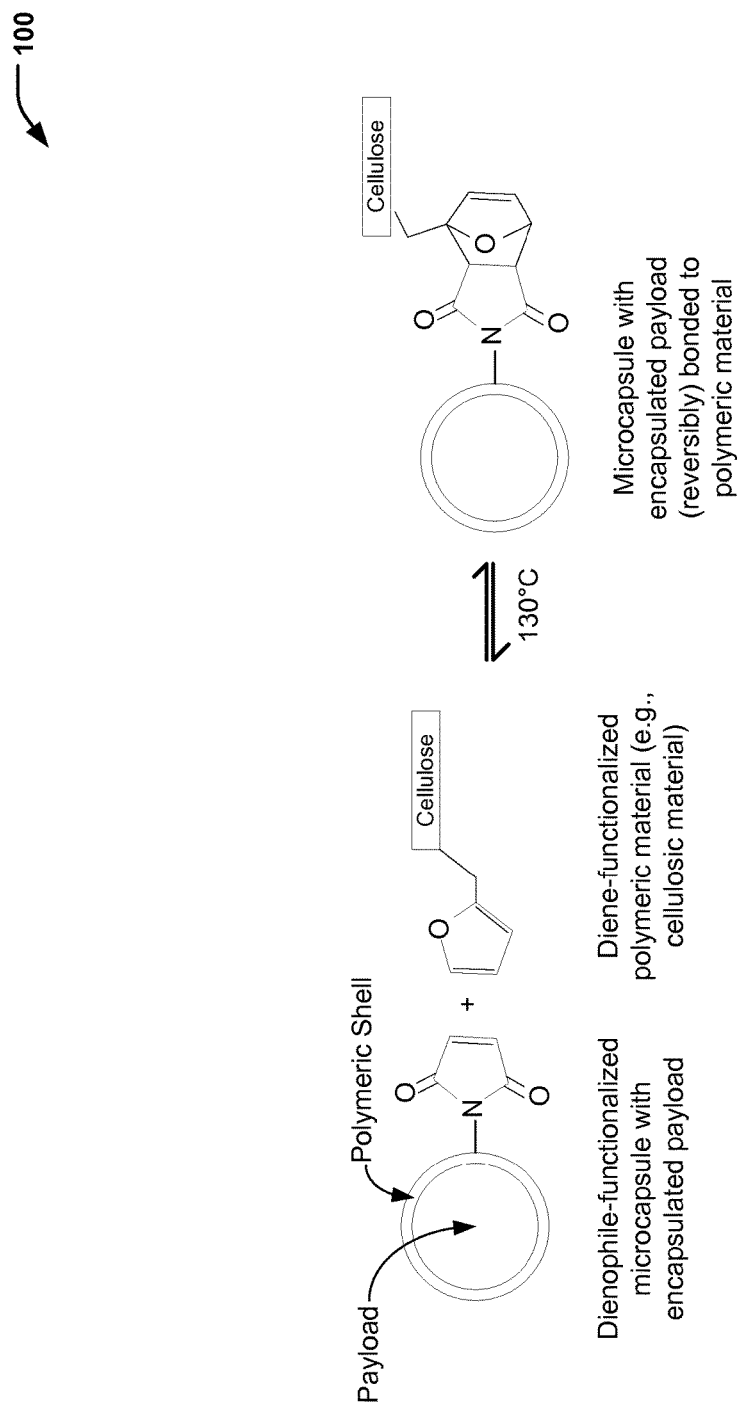
FIG. 1 is a chemical reaction diagram showing the preparation of a polymeric material with a microcapsule (having an encapsulated payload) that is (reversibly) bonded to a polymeric substrate, according to one embodiment.

The present disclosure relates to the formation of polymeric materials with microcapsules (having an encapsulated payload) that are (reversibly) bonded to a polymeric substrate (e.g., a fibrous substrate, such as a cellulosic material). In the present disclosure, a dienophile functional group of a dienophile-functionalized microcapsule may chemically react with a diene functional group of a diene-modified polymeric material (e.g., cotton) to bond the microcapsule to the polymeric material.

As used herein, the term "microcapsule" is used to refer to capsules that are in a range of about 10 microns to 1000 microns in diameter. However, it will be appreciated that the following disclosure may be applied to capsules having a smaller size (also referred to as "nanocapsules"). Further, the present disclosure may apply to natural polymeric materials (e.g., cellulosic fibers, such as cotton), synthetic polymeric materials (e.g., polyester fibers), or a combination thereof (e.g., a cotton/polyester blended fabric). In addition, the present disclosure may apply to flexible polymeric materials such as cotton fibers as well as relatively rigid polymeric materials (e.g., a thermoplastic, bamboo, etc.), among other alternatives.

In some cases, Diels-Alder chemistry may be used such that the microcapsule is reversibly bonded to the polymeric material (e.g., via a cyclic compound that is formed in a Diels-Alder reaction of an alkene functional group with a diene functional group). The reversible nature of the chemical reaction to bond the microcapsule to the polymeric material may allow the microcapsule to be removed and "reworked" to regenerate and/or change a payload. Thus, if microcapsules rupture and release the encapsulated payload(s) or if there is a desire to modify the payload(s), the microcapsules can be de-bonded from the polymeric material (e.g., via a retro Diels-Alder reaction). Another set of microcapsules (with the same or different payload) may then be (reversibly) bonded to the polymeric material, allowing the microcapsules to be "reworked" over time without replacing an underlying polymeric substrate.

In some implementations, natural polymers containing hydroxyl groups (such as cotton) are modified to incorporate diene functionalities off the surface. The combination of the dienophile functionalized microcapsules with the diene functionalized cotton allows for covalent bonding and associated adherence of the microcapsules to the cotton. When the combined material is strained, the microcapsules can rupture and thus release the payload. Using reversible chemistry, the broken microcapsules and/or other microcapsules can easily be reworked to regenerate or change the payload material.

The use of microcapsules allows for a homogenous distribution of the payload(s). The microcapsules can be incorporated at various volumes depending on the amount of payload(s) that may be desired. The microcapsules can be covalently bonded directly with the polymeric fibers. Microcapsules can be generated in a relatively homogenous size thus allowing for a controlled release of the payload per unit area. The protective outer layer of the microcapsule prevents leach out of the payload, making the microcapsules environmentally friendly.

FIG. 1 is a chemical reaction diagram 100 showing the preparation of a polymeric material with a microcapsule (having an encapsulated payload) that is (reversibly) bonded to a polymeric substrate, according to one embodiment. FIG. 1 illustrates that a payload may be encapsulated within a polymeric shell of a dienophile-functionalized microcapsule, as described further herein with respect to FIGS. 2 and 3. FIG. 1 further illustrates that a polymeric substrate (e.g., a cellulosic material in the example of FIG. 1) may be modified to include a diene functional group, as described further herein with respect to FIG. 4. In FIG. 1, the microcapsule (including the encapsulated payload) is (reversibly) bonded to the polymeric substrate via a chemical reaction of the dienophile functional group with the diene functional group.

In the example of FIG. 1, the left side of the chemical reaction diagram 100 illustrates a dienophile-functionalized microcapsule (having an encapsulated payload) and a diene-functionalized polymeric material. In the particular embodiment illustrated in FIG. 1, the polymeric material includes a fibrous substrate (e.g., a cellulosic material, such as cotton). The right side of the chemical reaction diagram 100 illustrates the microcapsule (with the encapsulated payload) bonded to the fibrous substrate. Thus, FIG. 1 illustrates an example of a (single) microcapsule having the encapsulated payload that is (reversibly) bonded to a polymeric material via a chemical reaction of a dienophile functional group with a diene functional group. While FIG. 1 illustrates a single dienophile functional group for a single microcapsule and a single diene functional group for the polymeric material, it will be appreciated that this is for illustrative purposes only. As illustrative, non-limiting examples, an available weight percentage of diene functionality may be within a range of about 1 to 10 weight percent of a total weight of a microcapsule, such as within a range of about 2 to 8 weight percent, about 3 to 7 weight percent, about 3.5 to 6 weight percent, or about 4 to 5 weight percent.

FIG. 1 illustrates that, in some cases, the chemical reaction of the dienophile functional group (of the functionalized microcapsule) with the diene functional group (of the functionalized polymeric material) may be a reversible reaction to reversibly bond the microcapsule to the polymeric material. In FIG. 1, the left side of the chemical reaction diagram 100 and the right side of the chemical reaction diagram 100 are separated by a forward arrow and a reverse arrow to indicate that the chemical reaction is a reversible reaction. In the particular embodiment illustrated in FIG. 1, a Diels-Alder reaction drives the reaction in a forward direction, and a retro Diels-Alder reaction drives the reaction in a reverse direction.

In the example illustrated in FIG. 1, the microcapsule having the encapsulated payload is reversibly bonded to the polymeric material via a cyclic compound (e.g., a bicyclic compound). In FIG. 1, the dienophile functional group of the dienophile-functionalized microcapsule is an alkene functional group (e.g., a cyclic alkene functional group). The chemical reaction of the alkene functional group with the diene functional group (e.g., a cyclic diene functional group) of the diene-functionalized polymeric material forms the bicyclic compound.

As a prophetic example, the microcapsules may be adhered to the polymeric material (e.g., a cellulosic material in FIG. 1) via covalent bonding using Diels-Alder chemistry. For example, the diene-functionalized polymeric material and the dienophile-functionalized microcapsules may be blended at elevated temperatures (e.g., at about 130° C.). As further described herein with respect to FIG. 2, a furan protected maleic anhydride may be de-protected when heated to a particular temperature (e.g., above about 125° C.). In the Diels-Alder chemistry illustrated in FIG. 1, the furan has been removed as a result of heating. After blending, a temperature may be reduced (e.g., to about 70° C.) for a time period of about 2 hours in order to allow the forward reaction to occur. The product with adhered microcapsules may be cooled (e.g., to room temperature) and excess reactants removed.

The right side of the chemical reaction diagram 100 of FIG. 1 illustrates that the microcapsule (having the encapsulated payload) is reversibly bonded to the polymeric material via the bicyclic compound. In the example of FIG. 1 in which the dienophile functional group is an alkene functional group, the reaction may be reversed via a retro Diels-Alder reaction. FIG. 1 illustrates a prophetic example in which the reaction may be reversed by heating (e.g., above about 130° C.) for a particular period of time to reverse the Diels-Alder reaction, allowing the microcapsules to detach from the cellulosic material. As further described herein with respect to FIG. 6, the reversible bonding of the microcapsule to the polymeric material may allow the microcapsule with the encapsulated payload to be de-bonded from the polymeric material (e.g., without the encapsulated payload being released from the microcapsule).

Thus, FIG. 1 illustrates an example of a polymeric material that includes a fibrous substrate (e.g., a cellulosic material) and a microcapsule (having an encapsulated payload) that is reversibly bonded to the fibrous substrate (e.g., via a cyclic compound). In FIG. 1, the microcapsule may be bonded to the fibrous substrate via a cyclic compound that is formed as a result of a chemical reaction of a dienophile functional group with a diene functional group to form the cyclic compound (e.g., via a Diels-Alder reaction). The dienophile functional group is associated with a dienophile-functionalized microcapsule (as described further herein with respect to FIGS. 2 and 3), and the diene functional group is associated with a diene-functionalized polymeric material (as described further herein with respect to FIG. 4). In the reversible reaction illustrated in FIG. 1, the microcapsule may be de-bonded from the polymeric material (e.g., via a retro Diels-Alder reaction). As described further herein with respect to FIG. 6, de-bonding the microcapsule may allow for another microcapsule (with the same payload or a different payload) to be bonded to the polymeric substrate.

Figure 2:
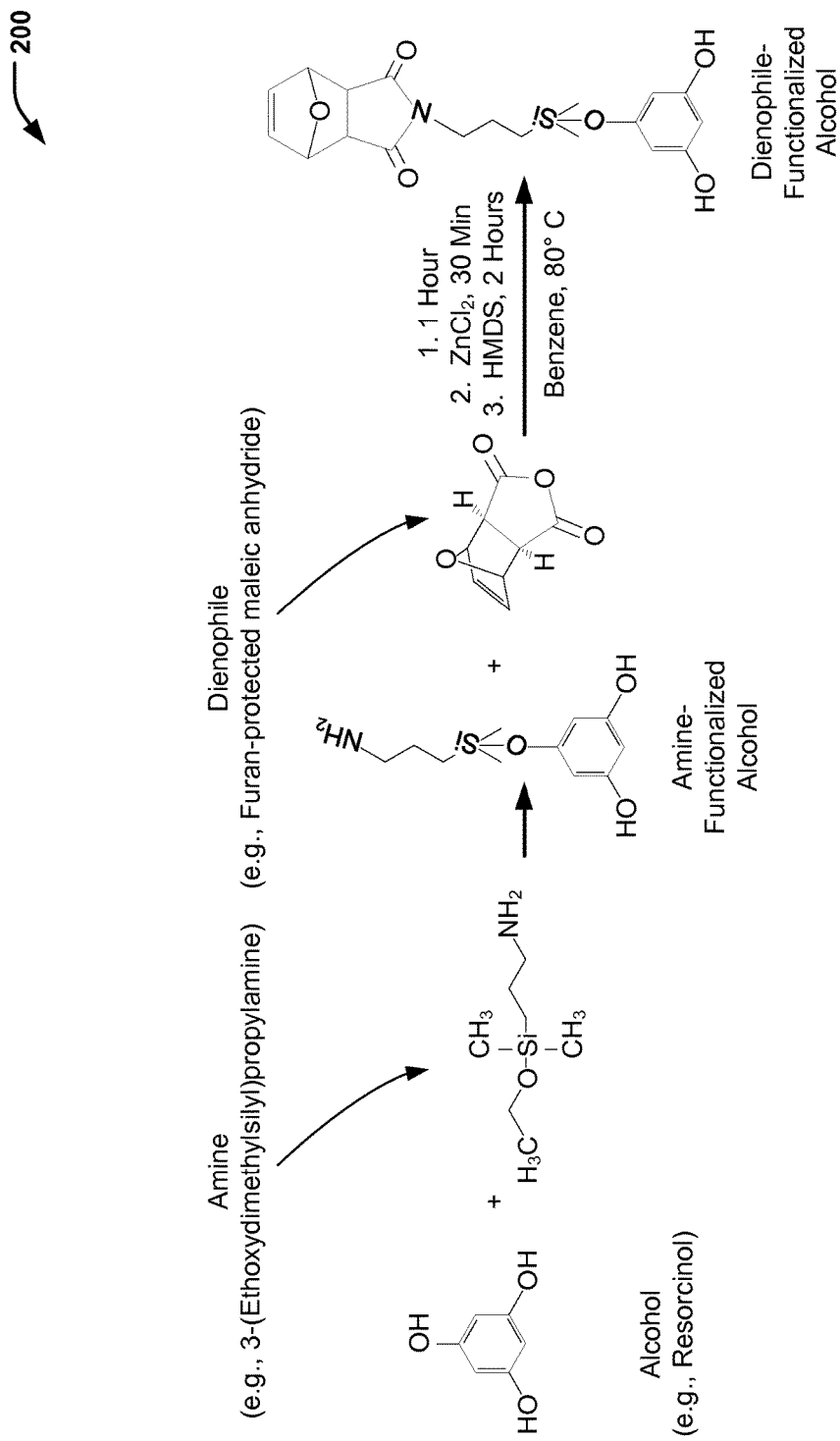
FIG. 2 is a chemical reaction diagram showing the preparation of a dienophile-functionalized alcohol for use in preparation of a dienophile-functionalized microcapsule (having an encapsulated payload) as illustrated in FIG. 3, according to one embodiment.

FIG. 2 is a chemical reaction diagram 200 showing the preparation of a dienophile-functionalized alcohol, according to one embodiment. The dienophile-functionalized alcohol of FIG. 2 may be used to prepare a dienophile-functionalized microcapsule (having an encapsulated payload), as illustrated and further described herein with respect to FIG. 3.

In the example illustrated in FIG. 2, an alcohol (e.g., resorcinol) is chemically reacted with an amine (e.g., 3-(Ethoxydimethylsilyl)propylamine) to form an amine-functionalized alcohol (e.g., amine-functionalized resorcinol). The amine-functionalized alcohol is chemically reacted with a dienophile material (e.g., a furan-protected maleic anhydride) to form a dienophile-functionalized alcohol (e.g., resorcinol with a dienophile functional group). In the example of FIG. 2, the furan protected maleic anhydride is 3,6-epoxy-1,2,3,6-tetrahydrophthalic anhydride. The protected maleic anhydride may be de-protected when heated to a particular temperature, as shown on the left side of the chemical reaction diagram 100 of FIG. 1.

FIG. 2 illustrates a prophetic example of reaction conditions to form dienophile-functionalized resorcinol. In FIG. 2, the amine-functionalized resorcinol, the furan protected maleic anhydride (3,6-epoxy-1,2,3,6-tetrahydrophthalic anhydride), and benzene are heated at about 80° C. for a time period of about 1 hour. Subsequently, $ZnCl_2$ may be added. After a time period of about 30 minutes, hexamethyldisiloxane (HDMS) may be added, and the reaction may continue for a time period of about 2 hours.

FIG. 2 illustrates that the chemical reaction of the amine functional group of the amine-functionalized resorcinol with the dienophile material (e.g., the furan protected maleic anhydride) results in replacement of oxygen with nitrogen to form a strained furan. Thus, the dienophile functional group of the dienophile-functionalized resorcinol of FIG. 2 is in protected form. For the Diels-Alder chemistry illustrated in FIG. 1, the furan is removed when heated (e.g., above about 125° C.).

Figure 3:
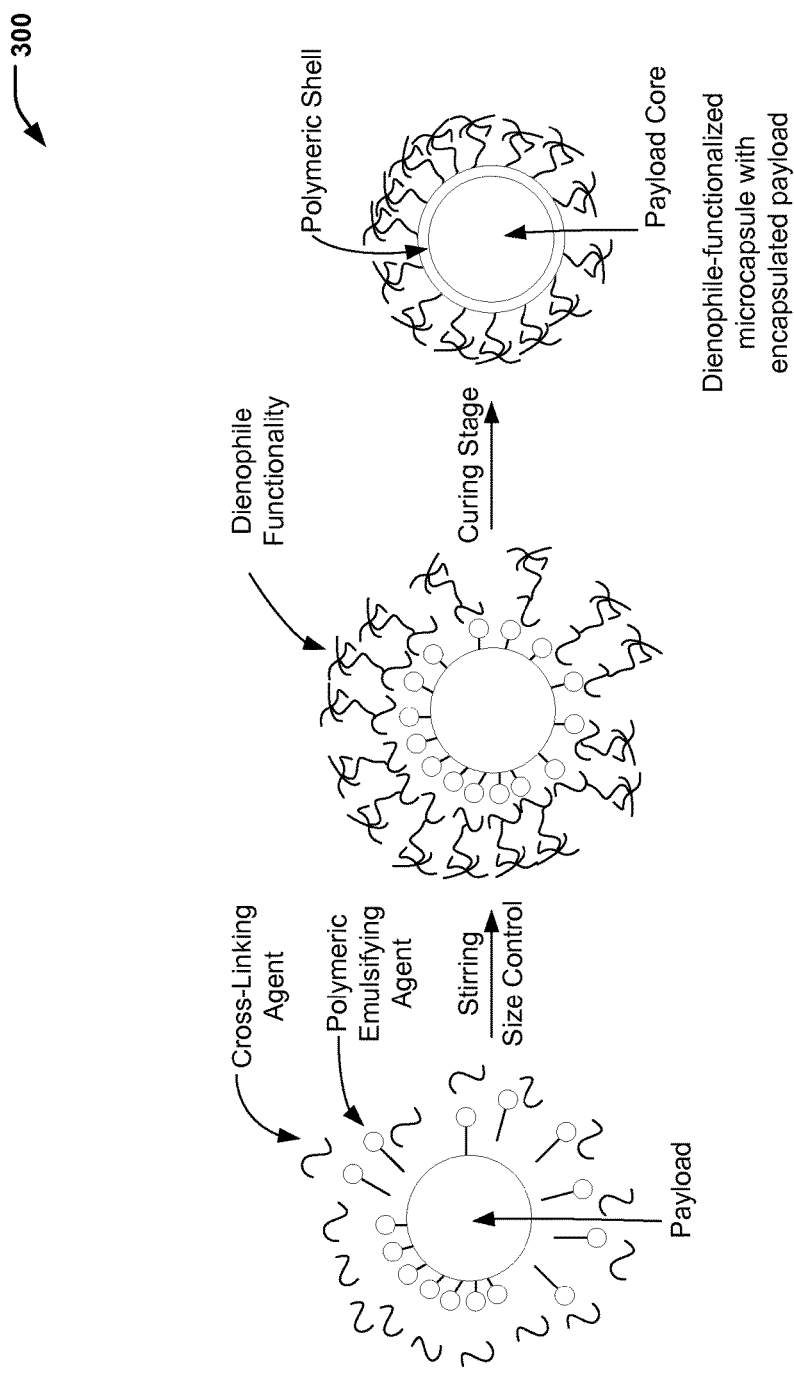
FIG. 3 is a chemical reaction diagram showing the preparation of a dienophile-functionalized microcapsule (having an encapsulated payload) using the dienophile-functionalized alcohol of FIG. 2, according to one embodiment.

As further described herein with respect to FIG. 3, the dienophile-functionalized alcohol that is formed via the chemical reactions illustrated in FIG. 2 may be used as a cross-linking agent when forming the dienophile-functionalized microcapsule with the encapsulated payload. For example, the dienophile-functionalized resorcinol may represent a portion of a total amount of resorcinol that may be used to form the polymeric shell of the microcapsule. As an illustrative, non-limiting example, the dienophile-functionalized alcohol may represent between about 10 to 20 weight percent of a total amount of resorcinol that is used, with a remaining 80 to 90 weight percent representing non-functionalized resorcinol.

Thus, FIG. 2 illustrates a particular embodiment of a process of producing a dienophile-functionalized alcohol (e.g., resorcinol). The dienophile-functionalized alcohol may represent at least a portion of the alcohol that is used during formation of a dienophile-functionalized microcapsule (having an encapsulated payload), as illustrated in FIG. 3.

FIG. 3 is a chemical reaction diagram 300 showing the preparation of a dienophile-functionalized microcapsule (having an encapsulated payload), according to one embodiment. In FIG. 3, payload filled microcapsules containing dienophile functionality are formed using an oil-in-water emulsion technique to create a protective polymeric shell around a payload core. The dienophile-functionalized alcohol illustrated in FIG. 2 may represent at least a portion of the cross-linking agent that is used to produce the dienophile-functionalized microcapsule of FIG. 3.

In the example of FIG. 3, a payload represents an oil phase that is dispersed into an aqueous continuous phase and stirred to begin an emulsion process. As illustrative, non-limiting examples, the payload (or multiple payloads) may include a perfume oil, a self-healing agent, a disinfectant, a repellant, or a combination thereof. It will be appreciated that various payload(s) may be selected to provide various functionalities for various applications. In FIG. 3, a cross-linking agent is reacted with a polymeric emulsifying agent to generate a capsule wall around the payload. Particle size may be controlled by adjusting a stir speed during the reaction. For example, a faster stir speed may result in formation (on average) of smaller ("finer") particles than a slower stir speed. FIG. 3 further illustrates that a curing stage may be used to complete the reaction between the cross-linking agent and the polymeric emulsifying agent to form the microcapsules (or nanocapsules, depending on a stir speed).

As illustrated in FIG. 1, the dienophile functional group(s) of the dienophile-functionalized microcapsule of FIG. 3 may chemically react with the diene functional group(s) of the diene-functionalized polymeric material to (reversibly) bond the microcapsule to the polymeric substrate.

In a prophetic example, dienophile-functionalized microcapsules may be prepared according to the following process. To a stirring aqueous solution containing an ethylene maleic anhydride (EMA) copolymer surfactant, urea, $NH_4Cl$, and resorcinol with a dienophile functionality may be added. A pH may be adjusted to about 3.5 by adding NaOH and HCl (or other acids/bases), followed by the addition of an emulsifying agent (e.g., a self-healing agent). The payload may be added with other ingredients, such as monomers and/or pre-polymers, stabilizers, solvents, viscosity modifiers, odorants, colorant/dyes, blowing agents, antioxidants, or co-catalysts, or a combination thereof. Formaldehyde may be added, which acts as a curing agent to complete the shell formation. The resulting microcapsules may be subsequently washed and sieved to remove unreacted material.

Figure 4:
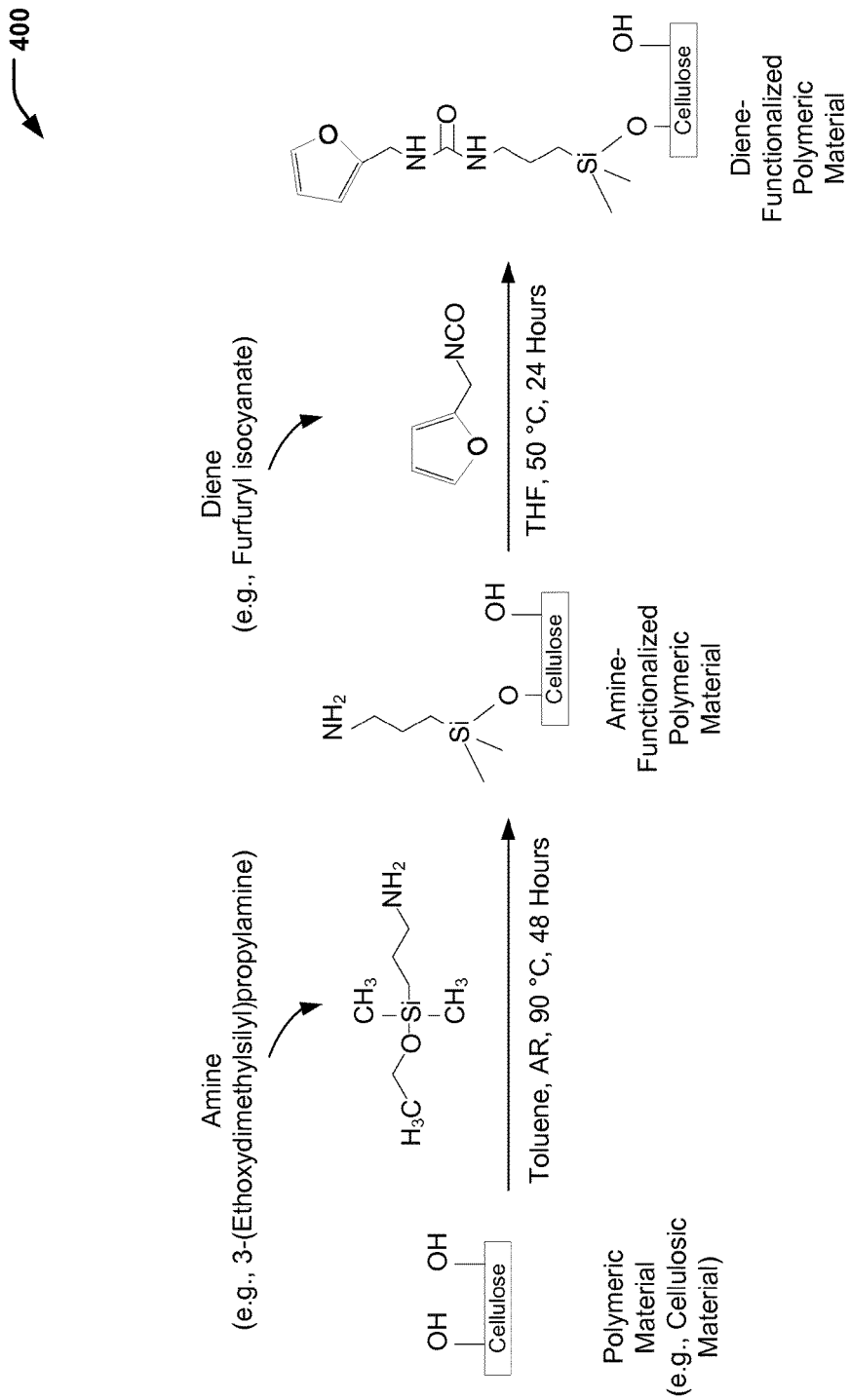
FIG. 4 is a chemical reaction diagram showing the preparation of a polymeric material with a diene functional group to be chemically reacted with a dienophile functional group of the dienophile-functionalized microcapsule of FIG. 3, according to one embodiment.

Thus, FIG. 3 illustrates a particular embodiment of a process of producing a dienophile-functionalized microcapsule (having an encapsulated payload). As illustrated and further described herein with respect to FIG. 1, a dienophile group of the dienophile-functionalized microcapsule produced according to the process illustrated in FIG. 3 may be reacted with a diene functional group of a diene-functionalized polymeric material to (reversibly) bond the microcapsule to the polymeric material. FIG. 4 illustrates a particular embodiment of a process of functionalizing a polymeric material (e.g., a cellulosic material) to include a diene functional group for reaction with the dienophile functional group.

FIG. 4 is a chemical reaction diagram 400 showing the preparation of a diene-functionalized polymeric substrate to be reacted with the dienophile-functionalized microcapsule formed in FIG. 3. As illustrated and further described herein with respect to FIG. 1, a diene functional group of the diene-functionalized polymeric material produced according to the process illustrated in FIG. 4 may be reacted with the dienophile functional group of the dienophile-functionalized microcapsule to (reversibly) bond the microcapsule to the polymeric material.

FIG. 4 illustrates a particular example in which a polymeric material having hydroxyl groups may be modified via amine chemistry, followed by a reaction with a diene to generate a polymeric surface with diene functionality. An example of a polymeric material with hydroxyl groups is cotton. Other polymeric material(s) may be selected by those skilled in the art. In the example of FIG. 4, furfuryl isocyanate is an example of a material that is used to provide the diene functionality.

FIG. 4 illustrates a prophetic example of reaction conditions associated with the preparation of a diene-modified polymeric material (e.g., a diene-modified cellulosic material). In the first chemical reaction shown in FIG. 4, cotton fibers (cellulose) are reacted with an amine (e.g., 3-(Ethoxydimethylsilyl)propylamine) in a solvent (e.g., toluene) at a temperature of about 90° C. for a time period of about 48 hours. After reaction, the product may be rinsed with water to remove residual material. In the second chemical reaction shown in FIG. 4, the amine-functionalized cotton is reacted with furfuryl isocyanate in tetrahydrofuran (THF) at a temperature of about 50° C. for a time period of about 24 hours. The resulting product is diene-modified cotton fibers.

In some cases, the amine functionalization may represent about 4 to 5 weight percent of the cellulosic material. In some cases, the weight percentage may be limited as a result of steric hindrance. It will be appreciated that a degree of amine functionalization may fall within a range of weight percentages, such as in a range of about 2 to 7 weight percent, in a range of about 3 to 6 weight percent, in a range of about 3.5 to about 5.5 weight percent, or in a range of about 4 to about 5 weight percent, among other alternative weight percentages.

Thus, FIG. 4 illustrates a particular embodiment of a process of functionalizing a polymeric material (e.g., a cellulosic material) to include a diene functional group for reaction with a dienophile functional group of a dienophile-functionalized microcapsule. As illustrated and further described herein with respect to FIG. 1, the microcapsule (having the encapsulated payload) may be (reversibly) bonded to the polymeric material via a chemical reaction of the diene functional group with the dienophile functional group.

Figure 5:
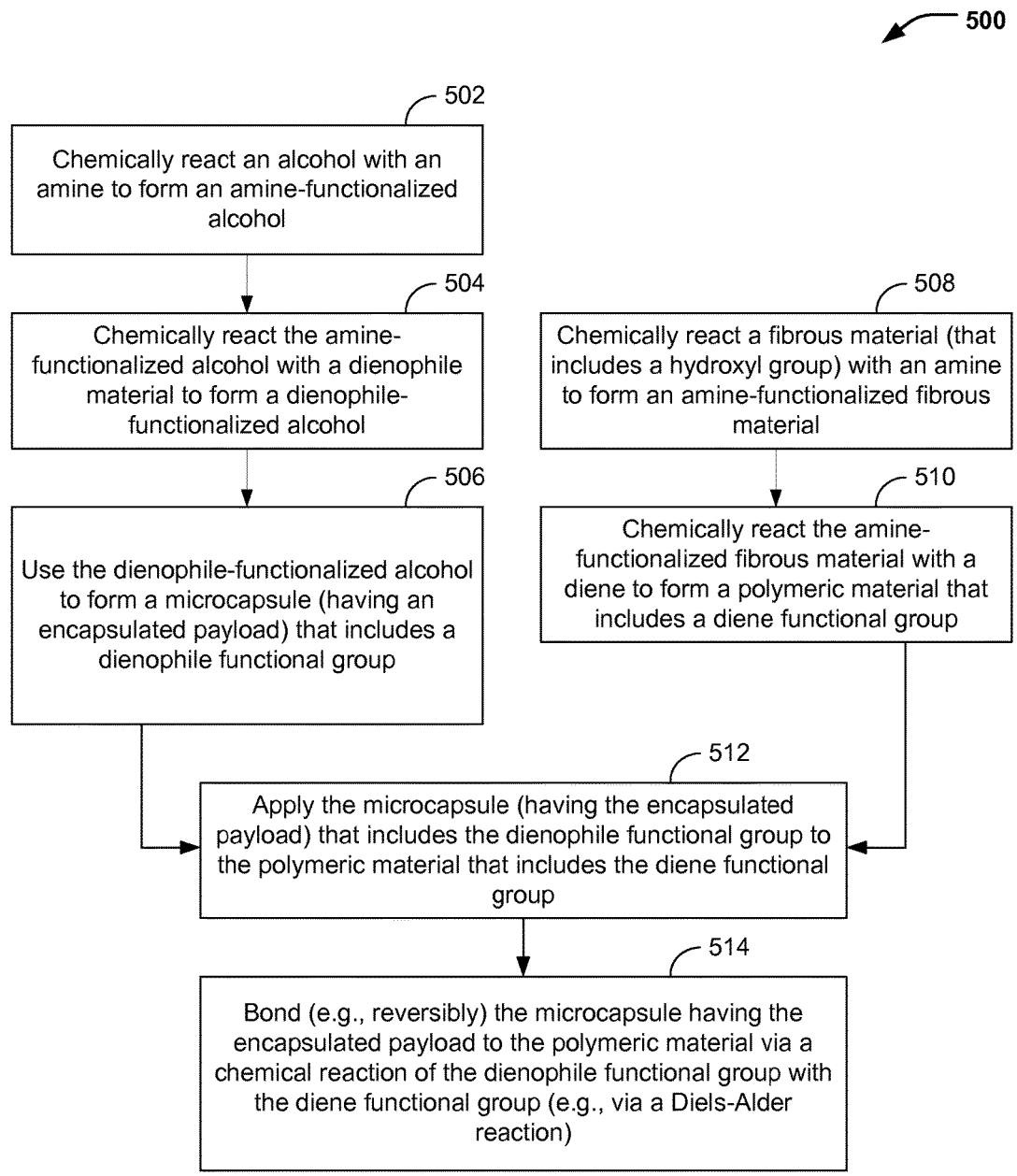
FIG. 5 is a flow diagram showing a particular embodiment of a method of bonding a microcapsule having an encapsulating payload to a polymeric material.

FIG. 5 is a flow diagram of a particular embodiment of a method 500 of forming a polymeric material that includes a microcapsule (having an encapsulated payload) that is bonded to the polymeric material. FIG. 5 illustrates an example of a process of producing a microcapsule that includes a dienophile functional group (as shown in FIG. 1 and further described herein with respect to FIGS. 2 and 3). FIG. 5 also illustrates an example of a process of producing a polymeric material that includes a diene functional group (as shown in FIG. 1 and further described herein with respect to FIG. 4). FIG. 5 further illustrates that the dienophile-functionalized microcapsule may be applied to the diene-functionalized polymeric material, and the microcapsule may be bonded to the polymeric material via a chemical reaction of the dienophile functional group with the diene functional group.

In the particular embodiment illustrated in FIG. 5, operations associated with an example process of producing a dienophile-functionalized microcapsule are identified as operations 502-506, while operations associated with producing a diene-functionalized polymeric material are illustrated as operations 508 and 510. It will be appreciated that the operations shown in FIG. 5 are for illustrative purposes only and that the chemical reactions may be performed in alternative orders, at alternative times, by a single entity or by multiple entities, or a combination thereof. As an example, one entity (e.g., a specialty chemical manufacturer) may produce the dienophile-functionalized microcapsule, while another entity (e.g., a synthetic fiber manufacturer, a clothing manufacturer, etc.) may produce the diene-functionalized polymeric material. Further, alternative or additional entities may perform the operations associated with bonding the microcapsule to the polymeric material via the chemical reaction of the dienophile functional group with the diene functional group (illustrated as operations 512 and 514).

The method 500 includes chemically reacting an alcohol with an amine to form an amine-functionalized alcohol, at 502. As an example, in the embodiment illustrated in FIG. 2, an alcohol (e.g., resorcinol) is chemically reacted with an amine (e.g., 3-(Ethoxydimethylsilyl)propylamine) to form an amine-functionalized alcohol (e.g., resorcinol with an amine functional group).

The method 500 includes chemically reacting the amine-functionalized alcohol with a dienophile material to form a dienophile-functionalized alcohol. As an example, in the embodiment illustrated in FIG. 2, the amine-functionalized alcohol (e.g., resorcinol with the amine functional group) is reacted with a dienophile material (e.g., a furan-protected maleic anhydride, such as 3,6-epoxy-1,2,3,6-tetrahydrophthalic anhydride) to form a dienophile-functionalized alcohol (e.g., resorcinol with a dienophile functional group).

The method 500 includes using the dienophile-functionalized alcohol to form a microcapsule (having an encapsulated payload) that includes a dienophile functional group, at 506. For example, the dienophile-functionalized alcohol formed in the embodiment illustrated in FIG. 2 (e.g., resorcinol with the dienophile functional group) may represent at least a portion of resorcinol that is used to form the dienophile-functionalized microcapsule illustrated in FIG. 3. As an illustrative, non-limiting example, the dienophile-functionalized resorcinol may represent about 10 to 20 weight percent of a total weight of resorcinol, while non-functionalized resorcinol may represent about 80 to 90 weight percent.

The method 500 includes chemically reacting a fibrous material (that includes a hydroxyl group) with an amine to form an amine-functionalized fibrous material, at 508. As an example, in the embodiment illustrated in FIG. 4, the cellulosic material (with two hydroxyl groups shown for illustrative purposes only) is reacted with an amine (e.g., 3-(Ethoxydimethylsilyl)propylamine) to form the amine-functionalized cellulosic material. FIG. 4 further illustrates that a portion of the hydroxyl groups of the cellulosic material may remain unreacted (e.g., as a result of steric hindrance). In some cases, the amine functionalization may represent about 4 to 5 weight percent of the cellulosic material.

The method 500 includes chemically reacting the amine-functionalized fibrous material with a diene to form a polymeric material that includes a diene functional group, at 510. As an example, in the embodiment illustrated in FIG. 4, the amine-functionalized cellulosic material is reacted with a diene (e.g., furfuryl isocyanate) to form the diene-functionalized cellulosic material.

The method 500 includes applying the microcapsule (having the encapsulated payload) that includes the dienophile-functional group to the polymeric material that includes the diene functional group, at 512. For example, referring to FIG. 1, the dienophile-functionalized microcapsule with the encapsulated payload may be applied to the diene-functionalized polymeric material (e.g., cellulosic material).

The method 500 further includes (reversibly) bonding the microcapsule (having the encapsulated payload to the polymeric material via a chemical reaction of the dienophile functional group with the diene functional group (e.g., via a Diels-Alder reaction), at 514. For example, referring to FIG. 1, the microcapsule with the encapsulated payload may be (reversibly) bonded to the polymeric material via a cyclic compound that is formed as a result of a chemical reaction of the alkene functional group of the microcapsule with the diene functional group of the cellulosic material (e.g., via a Diels-Alder reaction). In the particular embodiment illustrated in FIG. 1, the alkene functional group is a cyclic alkene functional group, the diene functional group is a cyclic diene functional group, and the cyclic compound is a bicyclic compound.

While not shown in the example of FIG. 5, in some cases, the microcapsule may be de-bonded from the polymeric material via a retro Diels-Alder reaction. As further described herein with respect to FIG. 6, reversibly bonding the microcapsule to a polymeric material may allow the microcapsule to be removed and replaced with another microcapsule (that may contain the same payload or a different payload).

Thus, FIG. 5 illustrates various operations associated with bonding a microcapsule (having an encapsulated payload) to a polymeric material. In some cases, the same entity or multiple entities may perform one or more of the operations. As an example, one or more entities (e.g., one or more specialty chemical manufacturers) may perform the operations 502-506 to form the dienophile-functionalized microcapsule (having the encapsulated payload). Another entity (or entities) or the same entity (or entities) may perform the operations 508 and 510 to form the diene-functionalized polymeric material. As a further example, another entity (or entities) or the same entity (or entities) may perform the operations 512 and 514 to (reversibly) bond the microcapsule to the polymeric material.

Figure 6:
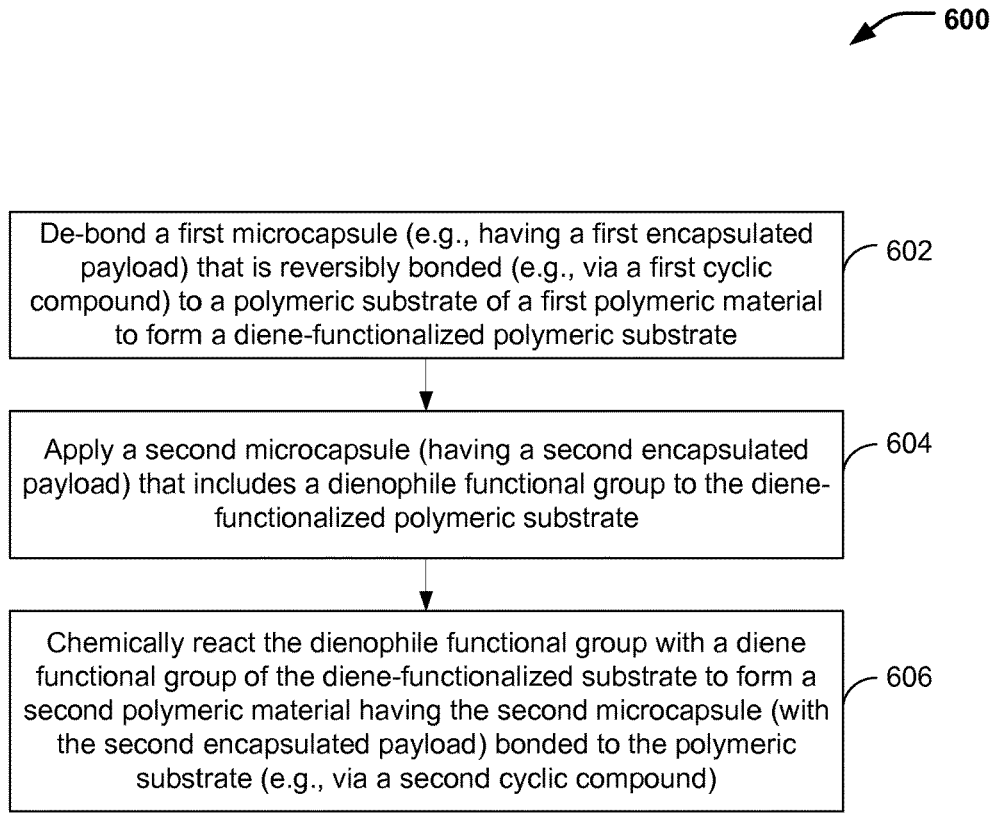
FIG. 6 is a flow diagram showing a particular embodiment of a method of modifying a first polymeric material to form a second polymeric material by replacing a first microcapsule with a second microcapsule.

FIG. 6 is a flow diagram of a particular embodiment of a method 600 of modifying a first polymeric material by replacing a first microcapsule (e.g., having a first encapsulated payload) that is reversibly bonded to the first polymeric material with a second microcapsule (having a second encapsulated payload) to form a second polymeric material.

The method 600 includes de-bonding a first microcapsule (e.g., including a first encapsulated payload) that is reversibly bonded to a polymeric substrate of a first polymeric material to form a diene-functionalized polymeric substrate, at 602. As an example, referring to FIG. 1, a retro Diels-Alder reaction may de-bond the first microcapsule from the polymeric material (e.g., a cellulosic material). In the example of FIG. 1, the first microcapsule is reversibly bonded to the polymeric substrate via a first cyclic compound (e.g., a bicyclic compound). In some cases, the first microcapsule may be de-bonded without a first encapsulated payload of the first microcapsule being released from the microcapsule.

The method 600 includes applying a second microcapsule (having a second encapsulated payload) that includes a dienophile functional group to the diene-functionalized polymeric substrate, at 604. In some cases, the first encapsulated payload may be different from the second encapsulated payload. In other cases, the first encapsulated payload may be the same as the second encapsulated payload. As an illustrative example, a first encapsulated payload may be released as a result of a microcapsule being ruptured. To illustrate, application of a threshold amount of mechanical strain to a fibrous material may result in release of the first encapsulated payload from the first microcapsule. In this case, the second microcapsule may allow for replacement of the payload that was released without modification to a polymeric substrate (e.g., cotton fibers). As another example, it may be desirable to replace/change an encapsulated payload in some cases. To illustrate, an entity (e.g., a manufacturer, an end user, etc.) may desire to replace a first perfume oil with a second perfume oil. In this case, the second microcapsule may allow the entity to change perfume oils without modification to the polymeric substrate (e.g., cotton fibers).

The method 600 further includes forming a second polymeric material via a chemical reaction of a dienophile functional group (of the second microcapsule) with a diene functional group (of the dienophile-functionalized polymeric substrate), at 606. The second microcapsule (having the second encapsulated payload) is bonded to the polymeric substrate via the chemical reaction of the dienophile functional group with the diene functional group. In some cases, the second microcapsule having the second encapsulated payload is reversibly bonded to the polymeric substrate via a second cyclic compound (e.g., a bicyclic compound) that is formed as a result of the chemical reaction of the dienophile functional group and the diene functional group of the diene-functionalized polymeric substrate.

Thus, FIG. 6 illustrates that the ability to de-bond (e.g., via a retro Diels-Alder reaction) a first microcapsule (that may have a first encapsulated payload) that is reversibly bonded to a polymeric substrate of a first polymeric material may allow for formation of a second polymeric material. After de-bonding the first microcapsule, a second microcapsule with a second encapsulated payload may be chemically bonded to the polymeric substrate. In some cases, the second encapsulated payload may be the same as the first encapsulated payload in order to replace a payload that is released as a result of the first microcapsule being ruptured. In other cases, the second encapsulated payload may be a different payload in order to provide alternative functionality when a microcapsule is ruptured.

The previous description of the disclosed embodiments is provided to enable any person skilled in the art to make or use the disclosed embodiments. Various modifications to these embodiments will be readily apparent to those skilled in the art, and the generic principles defined herein may be applied to other embodiments without departing from the scope of the disclosure. Thus, the present disclosure is not intended to be limited to the embodiments shown herein but is to be accorded the widest scope possible consistent with the principles and features as defined by the following claims.

The invention claimed is:

1. A process for bonding a microcapsule having an encapsulated payload to a polymeric material, the process comprising:
   forming a dienophile-functionalized alcohol by chemically reacting an alcohol with a first amine to form an amine-functionalized alcohol and chemically reacting the amine-functionalized alcohol with a dienophile to form a dienophile-functionalized alcohol, wherein:
      the alcohol includes resorcinol,
      the first amine includes 3-(Ethoxydimethylsilyl)propylamine, and
      the dienophile includes 3,6-epoxy-1,2,3,6-tetrahydrophthalic anhydride;
   forming a microcapsule having a shell encapsulating a payload, the shell having a dienophile functional group, by a chemical reaction of an aqueous solution comprising the dienophile-functionalized alcohol, ethylene maleic anhydride copolymer surfactant, urea, and $NH_4Cl$;
   applying the microcapsule to a polymeric material that includes a diene functional group; and
   bonding the shell of the microcapsule to the polymeric material via a chemical reaction of the dienophile functional group of the shell with the diene functional group of the polymeric material.

2. The process of claim 1, wherein the chemical reaction of the dienophile functional group with the diene functional group is a reversible reaction to reversibly bond the microcapsule having the encapsulated payload to the polymeric material.

3. The process of claim 2, wherein the microcapsule having the encapsulated payload is reversibly bonded to the polymeric material via a cyclic compound.

4. The process of claim 2, wherein:
   the chemical reaction of an alkene functional group of the dienophile with the diene functional group forms a cyclic compound;
   the microcapsule having the encapsulated payload is reversibly bonded to the polymeric material via the cyclic compound; and
   the reversible reaction is a retro Diels-Alder reaction.

5. The process of claim 4, wherein:
   the diene functional group is a cyclic diene functional group; and
   the cyclic compound is a bicyclic compound.

6. The process of claim 2, further comprising de-bonding the microcapsule with the encapsulated payload from the polymeric material without the encapsulated payload being released from the microcapsule.

7. The process of claim 1, further comprising:
   chemically reacting a fibrous material that includes a hydroxyl group with a second amine to form an amine-functionalized fibrous material; and
   chemically reacting the amine-functionalized fibrous material with a diene to form the polymeric material that includes the diene functional group.

8. The process of claim 7, wherein the second amine includes 3-(Ethoxydimethylsilyl)propylamine, and wherein the diene includes furfuryl isocyanate.

9. The process of claim 7, wherein the fibrous material includes a cellulosic material.

10. The process of claim 7, wherein application of a threshold amount of mechanical strain to the fibrous material results in release of the encapsulated payload from the microcapsule.

11. The process of claim 1, wherein the encapsulated payload includes a perfume oil, a self-healing agent, a disinfectant, or a repellant.

12. A process for bonding a microcapsule having an encapsulated payload to a polymeric material, the process comprising:
    forming a dienophile-functionalized alcohol by chemically reacting an alcohol with a first amine to form an amine-functionalized alcohol and chemically reacting the amine-functionalized alcohol with a dienophile to form a dienophile-functionalized alcohol, wherein:
       the alcohol includes resorcinol,
       the first amine includes 3-(Ethoxydimethylsilyl)propylamine, and
       the dienophile includes 3,6-epoxy-1,2,3,6-tetrahydrophthalic anhydride;
    forming a microcapsule having a shell encapsulating a payload, the shell having a dienophile functional group, by a chemical reaction of an aqueous solution comprising the dienophile-functionalized alcohol, ethylene maleic anhydride copolymer surfactant, urea, and $NH_4Cl$;
    applying the microcapsule to a polymeric material that includes a diene functional group; and
    bonding the shell of the microcapsule to the polymeric material via a chemical reaction of the dienophile functional group of the shell with the diene functional group of the polymeric material, wherein the chemical reaction of the dienophile functional group with the diene functional group is a reversible reaction to reversibly bond the microcapsule having the encapsulated payload to the polymeric material.

13. The process of claim 12, wherein the microcapsule having the encapsulated payload is reversibly bonded to the polymeric material via a cyclic compound.

14. The process of claim 12, wherein:
    the chemical reaction of an alkene functional group of the dienophile with the diene functional group forms a cyclic compound;
    the microcapsule having the encapsulated payload is reversibly bonded to the polymeric material via the cyclic compound; and
    the reversible reaction is a retro Diels-Alder reaction.

15. The process of claim 12, further comprising de-bonding the microcapsule with the encapsulated payload from the polymeric material without the encapsulated payload being released from the microcapsule.

16. The process of claim 12, further comprising:
    chemically reacting a fibrous material that includes a hydroxyl group with a second amine to form an amine-functionalized fibrous material; and chemically reacting the amine-functionalized fibrous material with a diene to form the polymeric material that includes the diene functional group.

17. The process of claim 16, wherein the second amine includes 3-(Ethoxydimethylsilyl)propylamine, and wherein the diene includes furfuryl isocyanate.

18. The process of claim 12, wherein the encapsulated payload includes a perfume oil, a self-healing agent, a disinfectant, or a repellant.

19. A process for bonding a microcapsule having an encapsulated payload to a polymeric material, the process comprising:
  forming a dienophile-functionalized alcohol by chemically reacting an alcohol with a first amine to form an amine-functionalized alcohol and chemically reacting the amine-functionalized alcohol with a dienophile to form a dienophile-functionalized alcohol, wherein:
    the alcohol includes resorcinol,
    the first amine includes 3-(Ethoxydimethylsilyl)propylamine, and
    the dienophile includes 3,6-epoxy-1,2,3,6-tetrahydrophthalic anhydride;
  forming a microcapsule having a shell encapsulating a payload, the shell having a dienophile functional group, by a chemical reaction of an aqueous solution comprising the dienophile-functionalized alcohol, ethylene maleic anhydride copolymer surfactant, urea, and $NH_4Cl$;
  applying the microcapsule to a polymeric material that includes a diene functional group;
  chemically reacting a fibrous material that includes a hydroxyl group with a second amine to form an amine-functionalized fibrous material;
  chemically reacting the amine-functionalized fibrous material with a diene to form the polymeric material that includes the diene functional group; and
  bonding the shell of the microcapsule to the polymeric material via a chemical reaction of the dienophile functional group of the shell with the diene functional group of the polymeric material, wherein the chemical reaction of the dienophile functional group with the diene functional group is a reversible reaction to reversibly bond the microcapsule having the encapsulated payload to the polymeric material.

20. The process of claim 19, wherein:

the chemical reaction of an alkene functional group of the dienophile with the diene functional group forms a cyclic compound;

the microcapsule having the encapsulated payload is reversibly bonded to the polymeric material via the cyclic compound; and the reversible reaction is a retro Diels-Alder reaction.

* * * * *